US006964777B2

(12) United States Patent
Klose et al.

(10) Patent No.: US 6,964,777 B2
(45) **Date of Patent: *Nov. 15, 2005**

(54) TRANSDERMAL DELIVERY OF ANTIANXIETY AGENTS

(75) Inventors: Kathryn Traci-Jane Klose, Chelsea (AU); Ennio La Guardia, East Coburg (AU); Timothy Matthias Morgan, Carlton North (AU); Barrie Charles Finnin, Glen Iris (AU); Barry Leonard Reed, Strathmore (AU)

(73) Assignee: Acrux DDS PTY LTD, Victoria (AU)

(*) Notice: Subject to any disclaimer, the term of this patent is extended or adjusted under 35 U.S.C. 154(b) by 147 days.

This patent is subject to a terminal disclaimer.

(21) Appl. No.: 10/428,017

(22) Filed: May 2, 2003

(65) Prior Publication Data

US 2004/0009214 A1 Jan. 15, 2004

Related U.S. Application Data

(60) Continuation-in-part of application No. 09/910,780, filed on Jul. 24, 2001, now Pat. No. 6,818,226, which is a division of application No. 09/125,436, filed as application No. PCT/AU97/00091 on Feb. 19, 1997, now Pat. No. 6,299,900.

(30) Foreign Application Priority Data

Feb. 19, 1996 (AU) ........................................... PN 8144

(51) Int. Cl.[7] ................................................ A61F 13/02
(52) U.S. Cl. ........................ 424/448; 424/449; 514/974
(58) Field of Search ................................ 424/448, 449; 514/974

(56) References Cited

U.S. PATENT DOCUMENTS

| | | | |
|---|---|---|---|
| 3,989,816 A | | 11/1976 | Rajadhyaksha |
| 4,299,826 A | | 11/1981 | Luedders |
| 4,440,777 A | | 4/1984 | Zupan |
| 4,557,934 A | | 12/1985 | Cooper |
| 4,704,406 A | | 11/1987 | Stanislaus et al. |
| 4,820,724 A | | 4/1989 | Nimni |
| 4,954,487 A | | 9/1990 | Cooper et al. |
| 5,034,386 A | | 7/1991 | Peck et al. |
| 5,036,100 A | | 7/1991 | Deboeck et al. |
| 5,082,656 A | * | 1/1992 | Hui et al. ..................... 514/24 |
| 5,082,866 A | | 1/1992 | Wong et al. |
| 5,122,519 A | | 6/1992 | Ritter |
| 5,256,647 A | | 10/1993 | Minaskanian et al. |
| 5,487,898 A | | 1/1996 | Lu et al. |
| 6,299,900 B1 | * | 10/2001 | Reed et al. ................. 424/449 |

FOREIGN PATENT DOCUMENTS

| | | |
|---|---|---|
| AU | 30258/89 | 9/1989 |
| AU | 49984/1990 | 9/1989 |

(Continued)

OTHER PUBLICATIONS

R.J. Feldmann et al., "Arch Derm", vol. 94, *Percutaneous Penetration of 14C Hydrocortisone in Man*, pp. 649–651 (Nov. 1966).

(Continued)

*Primary Examiner*—Shelley A. Dodson
*Assistant Examiner*—Konata M. George
(74) *Attorney, Agent, or Firm*—Foley & Lardner LLP

(57) ABSTRACT

The present invention provides a transdermal drug delivery system which comprises: a therapeutically effective amount of an antianxiety agent; at least one dermal penetration enhancer, which is a safe skin-tolerant ester sunscreen ester; and at least one volatile liquid. The invention also provides a method for administering at least one systemic acting antianxiety agent to an animal which comprises applying an effective amount of the antianxiety agent in the form of the drug delivery system of the present invention.

20 Claims, 1 Drawing Sheet

FOREIGN PATENT DOCUMENTS

Figure 1:
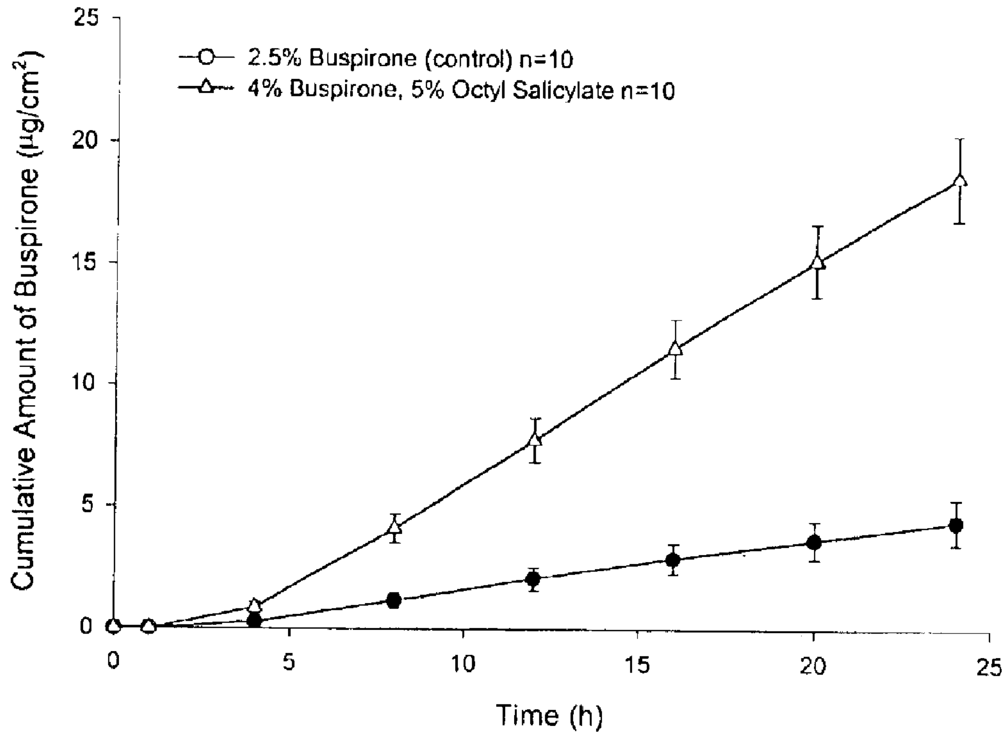

| | | |
|---|---|---|
| AU | 91413/91 | 6/1992 |
| DE | 43 34 553 | 4/1995 |
| EP | 189 861 | 8/1986 |
| JP | 61-268631 | 11/1986 |
| WO | 92/19271 | 11/1992 |
| WO | 96/30000 | 10/1996 |

OTHER PUBLICATIONS

M.F. Coldman et al., "Journal of Pharmaceutical Sciences", vol. 58, No. 9, *Enhancement of Percutaneous Absorption by the Use of Volatile Nonvolatile Systems and Vehicles*, pp. 1098–1102 (Sep. 1969).

P.P. Bhatt et al., "International Journal of Pharmaceutics" 50, *Finite dose transport of drugs in liquid formulations through stratum corneum: analytical solution to a diffusion model*, pp. 197–203 (1989).

Nimnl, U.S. Appl. No. 4,820,742, Internet: www.patents.ibm.com/fegi–bin/any2htm Document, *Dual Phase Solvent Carrier System*, pp. 3, 4 and 6 out of 7 pages.

* cited by examiner

TRANSDERMAL DELIVERY OF ANTIANXIETY AGENTS

This application is a continuation-in-part of U.S. patent application Ser. No. 09/910,780, filed Jul. 24, 2001, now U.S. Pat. No. 6,818,226 which is a divisional of Ser. No. 09/125,436, now U.S. Pat. No. 6,299,900, filed Dec. 18, 1998 as the U.S. national stage application of PCT application PCT/AU97/00091, filed Feb. 19, 1997. The entire contents of each of U.S. patent application Ser. No. 09/910,780, U.S. Pat. No. 6,299,900, and PCT application PCT/AU97/00091 are incorporated herein by reference, and priority to each is claimed under 35 U.S.C. § 119 and/or § 120.

FIELD OF THE INVENTION

The present invention relates to transdermal drug delivery. More specifically, the invention relates to a topical absorption/penetration enhancing agent for use in the delivery of antianxiety agents and antianxiety agent derivatives to an animal, including a human. The invention also relates to a system for the non-occlusive delivery to an animal of antianxiety agents and antianxiety agent derivatives across a dermal surface of the animal. Transdermal drug formulations of the present invention may be used for systemic delivery.

BACKGROUND OF THE INVENTION

There is a constant need for methods for the safe and effective administration of physiologically active agents, such as antianxiety agents. For many medications it is important that the administration regime is as simple and non-invasive as possible in order to maintain a high level of compliance by a patient. Oral administration is one administration regime that is commonly used because it is a relatively simple regime to follow. However, the oral administration route is also complicated because of complications associated with gastrointestinal irritation and with drug metabolism in the liver. Pre- and post-systemic metabolism is particularly important for the azapirone antianxiety agents such as buspirone which has a low absolute oral bioavailability of approximately 4% and a short pharmacokinetic half-life of approximately 2.5 hours (Clin. Pharmacokinetic. 36(4):277–287, April 1999). Consequently normal oral administration of buspirone requires multiple daily dosing which leads to reduced patient compliance.

Administration of physiologically active agents through the skin ('transdermal drug delivery') has received increased attention because it not only provides a relatively simple dosage regime but it also provides a relatively slow and controlled route for release of a physiologically active agent into the systemic circulation. However, transdermal drug delivery is complicated by the fact that the skin behaves as a natural barrier and therefore transport of agents through the skin is a complex mechanism.

Structurally, the skin consists of two principle parts, a relatively thin outermost layer (the 'epidermis') and a thicker inner region (the 'dermis'). The outermost layer of the epidermis (the 'stratum corneum') consists of flattened dead cells which are filled with keratin. The region between the flattened dead cells of the stratum corneum are filled with lipids which form lamellar phases that are responsible for the natural barrier properties of the skin.

For effective transdermal delivery of a physiologically active agent that is applied to the surface of the skin ('topical application'), the agent must be partitioned firstly from the vehicle into the stratum corneum, it must typically then be diffused within the stratum corneum before being partitioned from the stratum corneum to the viable epidermis and then into the dermal circulation.

To overcome some of the problems with transdermal delivery that are associated with transport across the dermal layers ('percutaneous absorption'), physiologically active agents are commonly formulated with incorporation of one or more dermal penetration enhancers (Finnin and Morgan, J. Pharm. Sci., Vol 88, No. 10, October 1999, pp. 755–758) which are often lipophilic chemicals that readily partition into the stratum corneum whereupon they exert their effects on improving the transport of drugs across the skin barrier.

There is a need for improvements in the transdermal delivery of antianxiety agents.

SUMMARY OF THE INVENTION

According to the present invention there is provided a transdermal drug delivery system comprising:

(a) a therapeutically effective amount of an antianxiety agent;

(b) at least one dermal penetration enhancer, which is a safe skin-tolerant ester sunscreen of formula (I):

(I)

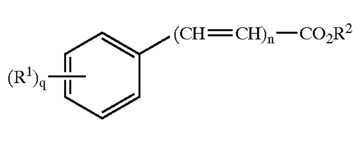

wherein $R^1$ is hydrogen, lower alkyl, lower alkoxy, halide, hydroxy or $NR^3$ $R^4$;

$R^2$ is a $C_8$ to $C_{18}$ alkyl;

$R^3$ and $R^4$ are each independently hydrogen, lower alkyl or $R^3$ and $R^4$ together with the nitrogen atom to which they are attached form a 5- or 6-membered heterocyclic ring;

n is 0 or 1, and q is 1 or 2, wherein, when n is 0 and $R^1$ is $NR^3R^4$, then $NR^3R^4$ is para-substituted and wherein said dermal penetration enhancer is present in an amount of from about 10 to about 10,000 wt % based on the weight of the hormone; and (c) at least one volatile liquid.

In addition to providing improved percutaneous absorption efficiency, the composition of the invention may also provide lower irritancy than some other more occlusive delivery systems such as transdermal patches, because the composition is non-occlusive to the skin.

More preferably the dermal penetration enhancer is selected from the group consisting of a $C_8$ to $C_{18}$ alkyl para-aminobenzoate, $C_8$ to $C_{18}$ alkyl dimethyl-para-aminobenzoate, $C_8$ to $C_{18}$ alkyl cinnamate, $C_8$ to $C_{18}$ alkyl methoxycinnamate or $C_8$ to $C_{18}$ alkyl salicylate. Most preferably the dermal penetration enhancer is octyl salicylate (2-ethylhexyl salicylate, octisalate), octyl dimethyl para-aminobenzoate or octyl para-methoxycinnamate (Padimate O).

The drug delivery systems according to the invention may comprise one or more antianxiety agents together with the penetration enhancer incorporated into a dosage form for topical application to the skin of animals.

Suitable dosage forms include creams, lotions, gels, ointments, mousses, sprays, aerosols, or any one of a variety of transdermal devices for use in the continuous administration of systematically active drugs by absorption through the skin. Some examples of suitable vehicles are given in U.S. Pat. Nos. 3,598,122, 3,598,123, 3,742,951, 3,814,097, 3,921,636, 3,993,072, 3,993,073, 3,996,934, 4,031,894, 4,060,084, 4,069,307, 4,201,211, 4,230,105, 4,292,299, 4,292,303, 5,323,769, 5,023,085, 5,474,783, 4,941,880 and 4,077,407. These disclosures are thus hereby incorporated herein by reference.

Optionally the drug delivery system may contain pharmaceutical compounding agents, such as one or more thickening agents such as cellulosic thickening agents, ethylcellulose, hydroxypropyl cellulose, hydroxypropyl methylcellulose, povidone, polyacrylic acids such as carbopol, Sepigel® (polyacrylamide/isoparaffin/laureth-7), the Gantrez® series of polymethyl vinyl ether/maleic anhydride copolymers such as the butyl ester of PVM/MA copolymer Gantrez® A-425, and any thickening agent known in the art that has good compatibility with the volatile liquid and enhancers of the present invention.

Preferred antianxiety agents of the present invention include at least one of an azapirone, such as buspirone, or others such as those disclosed in U.S. Pat. No. 5,837,280; benzodiazepines, such as alprazolam and triazolam; other GABA receptor agonists such as NGD-91-3; 5-HT 1A receptor antagonists such as DU-125530 and 5-HT 2A/2C antagonists such as deramciclane, also including salts and derivatives of the aforementioned antianxiety agents.

In one preferred form of the invention the drug delivery system comprises on a weight basis from about 0.1 to about 10% of the antianxiety agent, from about 0.1 to 10% of the at least one dermal penetration enhancer and from about 80 to 99.8% ethanol, isopropanol or mixture thereof.

In another preferred form of the invention the drug delivery system comprises, on a weight basis, from about 1 to 5% of an antianxiety agent, from about 1 to 5% of the dermal penetration enhancer, from about 45 to 90% ethanol, isopropanol or mixture thereof, 5 to 45% water; and optionally 0.5 to 5% of a thickening agent.

Whilst it is preferred that the antianxiety agent and penetration enhancer be delivered by simultaneous administration, the penetration enhancer may be applied before or after the application of the antianxiety agent, if desired.

The present invention also provides a method for administering at least one systemic or locally acting antianxiety agent to an animal which comprises applying an effective amount of the antianxiety agent in the form of the drug delivery system of the present invention.

Preferably the animal is a human but the invention also extends to the treatment of non-human animals.

Preferably the drug delivery system is not supersaturated with respect to the antianxiety agent. As the volatile liquid of the drug delivery system evaporates, the resulting non-volatile composition is rapidly driven into the dermal surface. It is possible that as the volatile liquid evaporates, the non-volatile dermal penetration enhancer becomes supersaturated with respect to the antianxiety agent. However, it is preferred that any supersaturation does not occur before transport of the resulting non-volatile composition across the epidermal surface has occurred.

It is most desirable that, after application of the drug delivery system, the volatile component of the delivery system evaporates and the area of skin to which the drug delivery system was applied becomes touch-dry. Preferably said area of skin becomes touch-dry within 10 minutes, more preferably within 3 minutes, most preferably within 1 minute.

The group of dermal penetration enhancing ester sunscreen compounds of the present invention are particularly suitable for transdermal delivery antianxiety agents through the skin of an animal. These dermal penetration enhancing compounds are of low toxicity to the skin and are excellent promoters of percutaneous absorption.

Preferred volatile liquids of the present invention include safe skin-tolerant solvents such as ethanol and isopropanol. An aerosol propellant, such as dimethyl ether, may constitute a volatile liquid for the purpose of the present invention.

Surprisingly the group of dermal penetration compounds identified enhance the absorption of antianxiety agents through the skin while avoiding the significant pharmacological disadvantages and toxicities of prior art enhancers. Additionally, the group of compounds of the invention surprisingly exhibit appreciable penetration into and substantivity for the outer layers of the skin, namely the stratum corneum which has previously presented a formidable barrier to percutaneous drug absorption.

In drug delivery systems according to the present invention a pharmaceutical compounding agent, co-solvent, surfactant, emulsifier, antioxidant, preservative, stabiliser, diluent or a mixture of two or more of said components may be incorporated in these systems as is appropriate to the particular route of administration and dosage form. The amount and type of components used should be compatible with the dermal penetration enhancers of this invention as well as with the antianxiety agent. A co-solvent or other standard adjuvant, such as a surfactant, may be required to maintain the antianxiety agent in solution or suspension at the desired concentration.

The pharmaceutical compounding agents can include paraffin oils, esters such as isopropyl myristate, ethanol, silicone oils and vegetable oils. These are preferably used in the range 1 to 50%. Surfactants such as ethoxylated fatty alcohols, glycerol mono stearate, phosphate esters, and other commonly used emulsifiers and surfactants preferably in the range of 0.1 to 10% may be used, as may be preservatives such as hydroxybenzoate esters for preservation of the compound preferably in amounts of 0.01% to 0.5%. Typical co-solvents and adjuvants may be ethyl alcohol, isopropyl alcohol, acetone, dimethyl ether and glycol ethers such as diethylene glycol mono ethyl ether. These may be used in amounts of 1 to 50%.

Because of the effect of the penetration enhancer of the invention, the dosage of the antianxiety agent may often be less than that conventionally used. It is proposed that, a dosage near the lower end of the useful range of the particular antianxiety agent may be employed initially and increased as indicated from the observed response if necessary.

The concentration of antianxiety agent used in the drug delivery system will depend on its properties and may be equivalent to that normally utilised for the particular antianxiety agent in conventional formulations. Both the amount antianxiety agent and the amount of penetration enhancer will be influenced by the type of effect desired.

Where it is desired to achieve higher systemic concentration of an antianxiety agent, proportionately higher concentrations of the enhancer of the invention may be required in the transdermal drug delivery system of the present invention, and the amount of antianxiety agent included in the composition should be sufficient to provide the blood level desired.

The concentration of absorption/penetration enhancer may be in the range from 10–10,000 weight percent of absorption/penetration enhancer based upon the weight of antianxiety agent. The ratio of penetration enhancer to antianxiety agent may vary considerably and will be governed as much as anything, by the pharmacological results that are required to be achieved. In principle, it is desirable that as little absorption enhancer as possible is used. On the other hand, for some antianxiety agents, it may well be that the upper range of 10,000% by weight will be required. It is preferred that the penetration enhancer and antianxiety agent are in approximately equal proportions.

A particular advantage of the drug delivery system of the present invention is that patient compliance is improved as the system does not occlude the skin. As a result local irritation and allergic sensitization problems arising from prolonged exposure of the skin to both the delivery system of occlusive transdermal patch devices and the adhesive used to affix these patches to the skin are reduced.

The following definitions apply through this description and the claims which follow.

The terms "percutaneous" and "transdermal" are used herein in the broadest sense to refer to being able to pass through unbroken skin.

The term "dermal penetration enhancer" is used herein in its broadest sense to refer to an agent which improves the rate of percutaneous transport of active agents across the skin or use and delivery of active agents to organisms such as animals, whether it be for local application or systemic delivery.

The term "non-occlusive" is used herein in its broadest sense to refer to not trapping or closing the skin to the atmosphere by means of a patch device, fixed reservoir, application chamber, tape, bandage, sticking plaster, or the like which remains on the skin at the site of application for a prolonged length of time.

The term "stratum corneum" is used herein in its broadest sense to refer to the outer layer of the skin, which is comprised of (approximately 15) layers of terminally differentiated keratinocytes made primarily of the proteinaceous material keratin arranged in a 'brick and mortar' fashion with the mortar being comprised of a lipid matrix made primarily from cholesterol, ceramides and long chain fatty acids. The stratum corneum creates the rate-limiting barrier for diffusion of the active agent across the skin.

The term "skin-depot" is used herein in its broadest sense to refer to a reservoir or deposit of active agent and dermal penetration enhancer within the stratum corneum, whether it be intra-cellular (within keratinocytes) or inter-cellular.

The term "volatile:non-volatile liquid vehicle" is used in the art to refer to a liquid pharmaceutical vehicle comprising a volatile liquid mixed with a non-volatile liquid vehicle, such as a dermal penetration enhancer. A system or vehicle comprising a volatile liquid mixed with a non-volatile dermal penetration enhancer when described herein is used in its broadest sense to include those systems known as volatile:non-volatile liquid vehicles.

Alkyl and alkoxy groups referred to herein may be either straight chain or branched. The term "lower alkyl" means alkyl groups containing from 1 to 5 carbon atoms. The term lower alkoxy has a similar meaning. The term "long chain alkyl" means alkyl groups containing from 5 to 18 carbon atoms, more preferably 6 to 18 carbon atoms. The term "halide" means fluoride, chloride, bromide or iodide. The term "heterocyclic ring" is herein defined to mean a ring of carbon atoms containing at least one hetero atom, and further the ring may be saturated or unsaturated to any allowable degree.

The term "sunscreen" is used herein in its broadest sense to refer to a chemical agent capable of filtering out ultraviolet light.

The drug delivery system of the present invention enables a wide range of antianxiety agents to be delivered through the skin to achieve a desired systemic effect. The drug delivery system preferably comprises the antianxiety agent intimately mixed with a non-volatile dermal penetration enhancer and a volatile liquid. Where the drug delivery system is applied to the skin, the antianxiety agent and non-volatile liquid are thermodynamically driven into the skin as the volatile liquid evaporates. Once within the skin the non-volatile liquid may either disrupt the lipid matrix and/or act as a solubilizer to allow an enhanced penetration rate of the antianxiety agent through the skin and into the subject being treated. In this way, the dermal penetration enhancer acts as a vehicle and many systemic active antianxiety agents are able to be transdermally administered to an animal.

It is believed that the non-volatile dermal penetration enhancer is readily absorbed into the stratum corneum in sufficient quantities to form a reservoir or depot of the dermal penetration enhancer within the stratum corneum. The dermal penetration enhancer also contains the antianxiety agent to be administered and as the dermal penetration enhancer crosses through the skin to form the skin-depot, the antianxiety agent contained therein is transported through the skin and contained within the depot. These depots are believed to form within the lipid matrix of the stratum corneum wherein the lipid matrix creates a rate-limiting barrier for diffusion of the antianxiety agent across the skin and allows the dermally administered antianxiety agent to be systemically released over a period of time, usually up to 24 hours.

Once the volatile liquid of the drug delivery system has evaporated, driving the mixture of non-volatile dermal penetration enhancer and antianxiety agent into the stratum corneum, the outer surface of the skin is then substantially free of antianxiety agent and non-volatile dermal penetration enhancer. Normal touching, wearing of clothes, rinsing or even washing of the skin will not, to any significant extent, affect delivery of the antianxiety agent or displace either the antianxiety agent or the non-volatile dermal penetration enhancer, once the volatile liquid has evaporated.

This is in contrast to prior-art systems where supersaturated solutions are used to increase the rate of drug permeation across the skin. Such supersaturated solutions are susceptible of ready precipitation and require stabilization, such as with polymers, or protection from external surfaces or objects which may effect nucleation.

The rate of absorption of the antianxiety agent via the stratum corneum is increased by the non-volatile dermal penetration enhancer. The antianxiety agent may be dissolved or suspended in the dermal penetration enhancer at the time when it is being transported from the surface of the skin and into the stratum corneum. The performance of the dermal penetration enhancer to deliver a desired antianxiety agent varies with differences in both the nature of the dermal penetration enhancer and the antianxiety agent. It is understood that different dermal penetration enhancers may need to be selected to be appropriate for delivery of various antianxiety agents.

Diseases or conditions that may be treated by using the drug delivery system and methods of the present invention include, but are not limited to, psychogenic symptomatologies due to the expanding understanding of the benefit of antianxiety agents for such purposes. For example, the treatment of conditions using azapirones such as buspirone as described in U.S. Pat. No. 5,837,280 are incorporated herein, as well as the therapeutic use of the drug delivery systems of the present invention for attention deficit hyperactivity disorder.

The drug delivery system of the present invention may be applied to the skin by means of an aerosol, spray, pump-pack, brush, swab, or other applicator. Preferably, the applicator provides either a fixed or variable metered dose application such as a metered dose aerosol, a stored-energy metered dose pump or a manual metered dose pump. Preferably the drug delivery system is applied to the skin of a human or animal covering a delivery surface area between about 10 and 800 $cm^2$, more preferably between about 10 and 400 $cm^2$, and most preferably between about 10 and 200 $cm^2$. The application is most preferably performed by means of a topical metered dose spray combined with an actuator nozzle shroud which together accurately control the amount and/or uniformity of the dose applied. One function of the shroud is to keep the nozzle at a pre-determined height above, and perpendicular to, the skin to which the drug delivery system is being applied. This function may also be achieved by means of a spacer-bar or the like. Another function of the shroud is to enclose the area above the skin in order to prevent or limit bounce-back and/or loss of the drug delivery system to the surrounding environment. Preferably the area of application defined by the shroud is substantially circular in shape.

The drug delivery system may be propelled by either pump pack or by the use of propellants such as hydrocarbons, hydro fluorocarbons, nitrogen, nitrous oxide, carbon dioxide or ethers, preferably dimethyl ether. The drug delivery system is preferably in a single phase system as this allows less complicated manufacture and ease of dose uniformity. It may also be necessary to apply a number of dosages on untreated skin to obtain the desired result.

DETAILED DESCRIPTION OF THE INVENTION

The invention will now be described with reference to the following examples and accompanying FIGURE. The examples and FIGURE are not to be construed as limiting the invention in any way. They are included to further illustrate the present invention and advantages thereof.

In the accompanying FIGURE:

FIG. 1 Shows the cumulative amount of buspirone penetrating across human epidermis ($\mu g/cm^2$) versus time (hours) for the transdermal spray composition 1A with or without the dermal penetration enhancer, octyl salicylate. Error bars represent Standard Error of the Mean (SEM).

In the examples, the effectiveness of the penetration enhancers are illustrated by measuring the skin penetration of formulations of a number antianxiety agents with the dermal penetration enhancers. Also, the skin penetration of antianxiety agents are measured with formulations of the antianxiety agents with common adjuvants, which serve as control formulations. The comparisons generally consist of measuring the relative penetration through shed snake skin of the various formulations. In every case, those formulations which contain the dermal penetration enhancers deliver more of the antianxiety agent through the skin than did corresponding control formulation.

EXAMPLE 1

Topical spray compositions

| Composition 1A | | Composition 1B | |
|---|---|---|---|
| Component | Amount | Component | Amount |
| Buspirone | 4% w/v* | Buspirone | 4% w/v |
| Octyl salicylate | 5% w/v | Padimate O | 6% w/v |
| Aqueous ethanol (95% v/v) | to 100 mL | Aqueous ethanol (95% v/v) | to 100 mL |

*equivalent to Buspirone 4.8% w/w

EXAMPLE 2

Enhanced skin penetration of buspirone base using octyl salicylate in a transdermal spray composition (Composition 1A).

As shown in FIG. 1 the addition of the safe sunscreen ester dermal penetration enhancer, octyl salicylate, surprisingly causes a marked 4-fold increase in the transdermal delivery of buspirone across the skin ($p<0.01$).

The diffusion experiments are performed using human epidermis as the model membrane. These experiments are performed over 24 h with stainless steel, flow-through diffusion cells based on those previously described, (Cooper, E. R. J. Pharm. Sci. 1984, 73, 1153–1156.) except that the cell is modified to increase the diffusional area to 1.0 $cm^2$. The formulations are applied using a finite dose technique (Franz, T. J. Curr. Probl. Dermatol. 1978, 7, 58–68.) to mimic clinical dosing conditions at an applied dose volume of 5 $\mu L/cm^2$. A piece of stainless steel wire mesh is placed directly below the skin in the receptor chamber of the diffusion cell to maintain a turbulent flow of receptor solution below the skin. The diffusion cells are maintained at a flow rate of approximately 1.0 $mL/cm^2/h$ by a microcassette peristaltic pump (Watson Marlow 505S, UK). The cells are kept at 32±0.5° C. by a heater bar and the samples are collected into appropriately sized plastic vials on an automated fraction collector (Isco Retriever II, Lincoln, Nev.) at specified intervals. The receptor solution (10% ethanol in water with 0.002% w/v sodium azide) maintains sink conditions beneath the skin.

Samples are analysed for buspirone directly by RP-HPLC using the following conditions: [Column-Waters Symmetry $C_{18}$ column (3.9×150 mm) with a 5 $\mu m$ support size; Mobile phase-20% Acetonitrile buffered with 0.01M $KH_2PO_4$, pH=2.80; Flow rate 1 mL/min; Absorbance-239 nm; and Injection volume-50 $\mu L$].

EXAMPLE 3

Topical gel compositions

| Composition 3A | | Composition 3B | |
|---|---|---|---|
| Component | Amount | Component | Amount |
| Buspirone | 2% w/v | Buspirone | 2% w/v |
| Octyl salicylate | 1% w/v | Padimate O | 2% w/v |
| Carbopol | 0.9% w/v | Carbopol | 0.9% w/v |
| 0.1N NaOH | 4.72% w/v | 0.1N NaOH | 4.72% w/v |

-continued

Topical gel compositions

| Composition 3A | | Composition 3B | |
|---|---|---|---|
| Component | Amount | Component | Amount |
| Aqueous ethanol (70% v/v) | to 100 mL | Aqueous ethanol (70% v/v) | to 100 mL |

EXAMPLE 4

Topical lotion compositions

| Composition 4A | | Composition 4B | |
|---|---|---|---|
| Component | Amount | Component | Amount |
| Buspirone | 2% w/v | Buspirone | 2% w/v |
| Octyl salicylate | 2.5% w/v | Padimate O | 3% w/v |
| Hydroxy propyl cellulose | 1.5% w/v | Ethyl cellulose | 1.5% w/v |
| Aqueous ethanol (90% v/v) | to 100 mL | Aqueous ethanol (90% v/v) | to 100 mL |

We claim:

1. A transdermal drug delivery system comprising:

(a) a therapeutically effective amount of an antianxiety agent;

(b) at least one dermal penetration enhancer, which is a safe skin-tolerant ester sunscreen of formula (I):

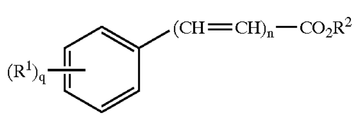

(I)

wherein $R^1$ is hydrogen, lower alkyl, lower alkoxy, halide, hydroxy or $NR^3$ $R^4$;

$R^2$ is a $C_8$ to $C_{18}$ alkyl;

$R^3$ and $R^4$ are each independently hydrogen, lower alkyl or $R^3$ and $R^4$ together with the nitrogen atom to which they are attached form a 5- or 6-membered heterocyclic ring;

n is 0 or 1, and q is 1 or 2, wherein, when n is 0 and $R^1$ is $NR^3R^4$, then $NR^3R^4$ is para-substituted, and wherein said dermal penetration enhancer is present in an amount of from about 10 to about 10,000 wt % based on the weight of the hormone; and (c) at least one volatile liquid.

2. The transdermal drug delivery system according to claim 1, wherein the dermal penetration enhancer is octyl salicylate.

3. The transdermal drug delivery system according to claim 1, wherein the volatile liquid selected from the group consisting of ethanol, isopropanol, and a mixture thereof.

4. The transdermal drug delivery system according to claim 1, comprising on a weight basis:

(a) from about 0.1 to about 10% of said antianxiety agent;

(b) from about 0.1 to about 10% of said at least one dermal penetration enhancer; and (c) from about 80 to about 99.8% of said volatile liquid.

5. The transdermal drug delivery system according to claim 1, wherein the antianxiety agent is selected from the group consisting of azapirones, GABA receptor agonists, 5-HT 1A receptor antagonists and 5-HT 2A/2C antagonists, including salts and derivatives of the aforementioned antianxiety agents.

6. The transdermal drug delivery system according to claim 5, wherein the antianxiety agent is buspirone.

7. The transdermal drug delivery system according to claim 6, comprising on a weight basis:

(a) from about 1 to about 6% buspirone;

(b) from about 1 to about 10% octyl salicylate; and (c) from about 84 to about 98% Alcohol USP (95% ethanol).

8. The transdermal drug delivery system according to claim 6, comprising on a weight basis:

(a) from about 1 to about 5% buspirone;

(b) from about 1 to about 5% octyl salicylate; and (c) from about 45 to about 90% of a volatile liquid selected from the group consisting of ethanol, isopropanol, and a mixture thereof;

(d) from about 5 to about 45% water; and (e) from about 0.5 to about 5% of a thickening agent.

9. The transdermal drug delivery system according to claim 5, wherein the antianxiety agent is selected from the group consisting of NGD-91-3, DU-125530 amd deramciclane.

10. The transdermal drug delivery system according to claim 1, wherein the antianxiety agent is a benzodiazepine.

11. The transdermal drug delivery system according to claim 10, wherein the benzodiazepine is triazolam.

12. The transdermal drug delivery system according to claim 1, wherein the antianxiety agent is alprazolam.

13. A method for administering at least one systemic acting antianxiety agent to an animal which comprises applying an effective amount of the antianxiety agent in the form of the drug delivery system according to claim 1.

14. The method according to claim 13, wherein the antianxiety agent is selected from the group consisting of azapirones, GABA receptor agonists, 5-HT 1A receptor antagonists and 5-HT 2A/2C antagonists, including salts and derivatives of the aforementioned antianxiety agents.

15. The method according to claim 13, wherein the antianxiety agent is a benzodiazepine.

16. The method according to claim 13, wherein the antianxiety agent is alprazolam.

17. The method according to claim 13, wherein the drug delivery system is applied to the skin of the animal covering a delivery surface area between about 10 and 800 $cm^2$.

18. The method according to claim 13, wherein the drug delivery system is applied to the skin of the animal covering a delivery surface area between about 10 and 400 $cm^2$.

19. The method according to claim 13, wherein the drug delivery system is applied to the skin of the animal covering a delivery surface area between about 10 and 200 $cm^2$.

20. The method according to claim 13, wherein the drug delivery system is applied using a fixed or variable metered dose applicator.

* * * * *